(12) United States Patent
Graham

(10) Patent No.: US 11,439,476 B2
(45) Date of Patent: Sep. 13, 2022

(54) MEDICAL DEVICE HANDLE LOCK

(71) Applicant: Gyrus ACMI, Inc., Westborough, MA (US)

(72) Inventor: Madeline C. Graham, Sammamish, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 232 days.

(21) Appl. No.: 16/333,733

(22) PCT Filed: Aug. 30, 2016

(86) PCT No.: PCT/US2016/049374
§ 371 (c)(1),
(2) Date: Mar. 15, 2019

(87) PCT Pub. No.: WO2018/044269
PCT Pub. Date: Mar. 8, 2018

(65) Prior Publication Data
US 2021/0282881 A1    Sep. 16, 2021

(51) Int. Cl.
*A61B 90/00* (2016.01)
*A61B 10/02* (2006.01)
*A61B 17/34* (2006.01)
*A61B 17/00* (2006.01)

(52) U.S. Cl.
CPC .......... *A61B 90/03* (2016.02); *A61B 10/0233* (2013.01); *A61B 17/3496* (2013.01); *A61B 90/08* (2016.02); *A61B 2010/0208* (2013.01); *A61B 2017/00477* (2013.01); *A61B 2090/034* (2016.02); *A61B 2090/0807* (2016.02); *A61B 2090/08021* (2016.02)

(58) Field of Classification Search
CPC ............ A61B 17/3401; A61B 17/3478; A61B 17/3496
See application file for complete search history.

(56) References Cited

U.S. PATENT DOCUMENTS

| | | | | |
|---|---|---|---|---|
| 5,064,414 | A | * | 11/1991 | Revane ............. A61M 25/0612 604/165.01 |
| 5,098,392 | A | * | 3/1992 | Fleischhacker ... A61M 25/0668 604/161 |
| 5,429,616 | A | * | 7/1995 | Schaffer ............ A61M 25/0606 604/167.06 |
| 5,437,645 | A | * | 8/1995 | Urban .................... A61B 17/34 604/165.02 |

(Continued)

*Primary Examiner* — Ryan J. Severson
(74) *Attorney, Agent, or Firm* — Schwegman Lundberg & Woessner, P.A.

(57) ABSTRACT

A medical instrument having a handle with a clamp that is configured to maintain the instrument in two different operational modes. The medical instrument includes a needle, a sheath, a sheath handle, a needle actuator and a locking device. The distal end of the needle actuator is connected to the proximal end of the needle. The distal end of the sheath handle is connected to the proximal end of the sheath. The locking device restricts distal movement of the needle actuator relative to the sheath handle when the medical device is placed in one of two operational states. In a deactivation state the distal end of the needle is housed within the distal end of the sheath. In an activation state the distal end of the needle is distal from the distal end of the sheath.

20 Claims, 6 Drawing Sheets

(56) References Cited

U.S. PATENT DOCUMENTS

| | | | | |
|---|---|---|---|---|
| 5,454,790 | A * | 10/1995 | Dubrul | A61M 25/0102 604/104 |
| 6,096,009 | A * | 8/2000 | Windheuser | A61M 25/0097 24/339 |
| 6,096,024 | A * | 8/2000 | Graves | A61M 39/1011 604/161 |
| D467,339 | S * | 12/2002 | Trask | D24/128 |
| 7,192,433 | B2 * | 3/2007 | Osypka | A61M 25/0668 604/164.05 |
| 7,556,617 | B2 * | 7/2009 | Voorhees, Jr. | A61M 25/0631 604/162 |
| 8,613,728 | B2 * | 12/2013 | Amisar | A61M 25/06 604/174 |
| 8,915,884 | B2 * | 12/2014 | Tal | A61M 25/0097 604/165.01 |
| 8,986,264 | B2 * | 3/2015 | Kimmel | A61M 39/1011 604/264 |
| 9,005,196 | B2 * | 4/2015 | Lingeman | A61B 17/22012 606/41 |
| 9,320,531 | B2 * | 4/2016 | Lingeman | A61B 18/26 |
| 9,326,756 | B2 * | 5/2016 | Stangenes | A61B 17/3478 |
| 9,358,039 | B2 * | 6/2016 | Kimmel | A61B 17/3478 |
| 9,775,633 | B2 * | 10/2017 | Lingeman | A61B 17/22012 |
| 10,010,343 | B2 * | 7/2018 | Bierman | A61M 25/0097 |
| 10,136,916 | B2 * | 11/2018 | Bierman | A61B 17/3423 |
| 10,201,265 | B2 * | 2/2019 | Dickhans | A61B 18/1492 |
| 10,499,980 | B2 * | 12/2019 | Shuman | A61B 18/1492 |
| 10,569,059 | B2 * | 2/2020 | Bierman | A61M 29/00 |
| 11,039,819 | B2 * | 6/2021 | Gonzalez | A61M 5/329 |
| 11,039,879 | B2 * | 6/2021 | Gonzalez | A61B 18/1477 |
| 2004/0092879 | A1 * | 5/2004 | Kraus | A61M 25/065 604/158 |
| 2004/0102789 | A1 * | 5/2004 | Baughman | A61F 2/011 606/99 |
| 2007/0270751 | A1 * | 11/2007 | Stangenes | A61B 17/00234 604/164.1 |
| 2009/0149857 | A1 * | 6/2009 | Culbert | A61B 17/1757 606/80 |
| 2011/0021994 | A1 * | 1/2011 | Anderson | A61M 25/0606 604/164.01 |
| 2013/0046297 | A1 * | 2/2013 | Lingeman | A61B 17/221 606/41 |
| 2014/0276764 | A1 * | 9/2014 | Shuman | A61B 18/1492 606/34 |
| 2015/0173784 | A1 * | 6/2015 | Lingeman | A61B 17/221 606/128 |
| 2016/0199133 | A1 * | 7/2016 | Lingeman | A61B 17/22012 606/14 |
| 2018/0271594 | A1 * | 9/2018 | Tyson | A61B 18/14 |
| 2021/0282881 | A1 * | 9/2021 | Graham | A61B 10/0233 |

* cited by examiner

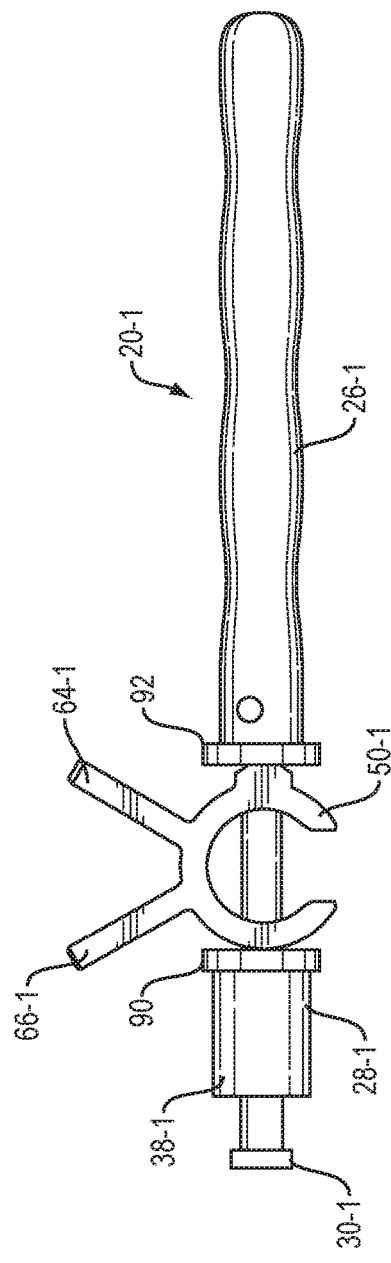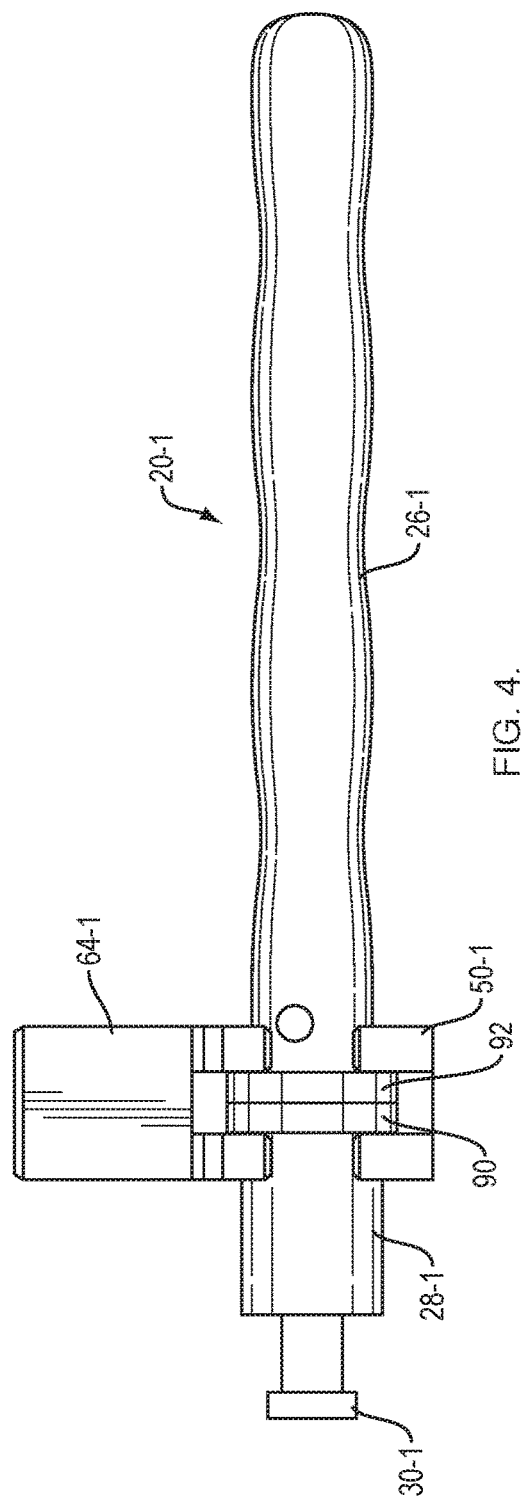

MEDICAL DEVICE HANDLE LOCK

PRIORITY CLAIM

The present invention claims the benefit of PCT/US16/49374.

FIELD

The present invention relates to medical device handles used for tissue sampling.

BACKGROUND

The statements in this section merely provide background information related to the present disclosure and may not constitute prior art.

Some handle designs for medical devices, such as those used with needles for collecting samples from target tissue, use simple cantilever springs, friction fits or O-rings. The earlier O-ring designs offer some "locking" ability with a groove to seat the O-ring. However, those grooves are generally shallow, which could also allow the needle to accidentally advance without the user's input, causing a potential safety issue or scope damage.

SUMMARY

The present invention provides an example medical instrument for sampling tissue. The example medical instrument includes a handle with a clamp that is configured to maintain the instrument in two different operational modes.

In accordance with aspects of the invention, an example medical device includes a needle, a sheath, a sheath handle, a needle actuator and a locking device. The distal end of the needle actuator is connected to the proximal end of the needle. The distal end of the sheath handle is connected to the proximal end of the sheath. The distal end of the needle actuator is connected to the proximal end of the needle. The locking device restricts distal movement of the needle actuator relative to the sheath handle when the medical device is placed in one of two operational states. A first one of the operational states is a deactivation state, where in the deactivation state the distal end of the needle is housed within the distal end of the sheath.

In accordance with further aspects of the invention, the locking device includes a clamping element configured to restrict proximal movement of the needle actuator relative to the sheath handle when the medical device is in a first one of the operational states and a spacing element configured to restrict distal movement of the needle actuator relative to the sheath handle when the medical device in a second one of the operational states. The first operational state is a needle actuation state—the distal end of the needle extends distally beyond the distal end of the sheath.

In accordance with other aspects of the invention, the clamping element includes a base section, a first pair of curved arms that extend from the base section along a first plane and a second pair of curved arms that extend from the base section along a second plane. The radius of curvature of all the arms is based on a shape of an exterior of the needle actuator and the sheath handle. An axis connecting a center of curvature of the first pair of curved arms and a center of curvature of the second pair of curved arms is perpendicular to the first and second planes.

In accordance with yet other aspects of the invention, the spacing element is configured to receive a shaft portion of the needle actuator within a gap between the first pair of curved arms and the second pair of curved arms.

In accordance with still other aspects of the invention, the locking device further comprises a handle component connected at least in part to the base section, wherein activation of the handle component translates to an expansion motion of the first ones of the first and second pairs of curved arms from the second ones of the first and second pairs of curved arms.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings:

FIG. 1-2 illustrates a cross-sectional view of the aspiration device of FIG. 1-1 in an activated state;

FIG. 2-1 illustrates a perspective view of a clamp and spacer device used with the aspiration device of FIGS. 1-1 and 1-2 in accordance with principles of the present invention;

FIG. 2-2 illustrates a side view of the device of FIG. 2-1;

FIG. 2-3 illustrates a side view of the device of FIG. 2-1;

FIG. 2-4 illustrates a side view of the device of FIG. 2-1;

FIG. 3 illustrates a side view of a clamp and spacer device interacting with an aspiration device in accordance with principles of the present invention;

FIG. 4 illustrates a side view of the clamp and spacer device shown in FIG. 3 interacting with the aspiration device in accordance with principles of the present invention;

DETAILED DESCRIPTION

The following description is merely exemplary in nature and is not intended to limit the present disclosure, application, or uses.

Figure 1:
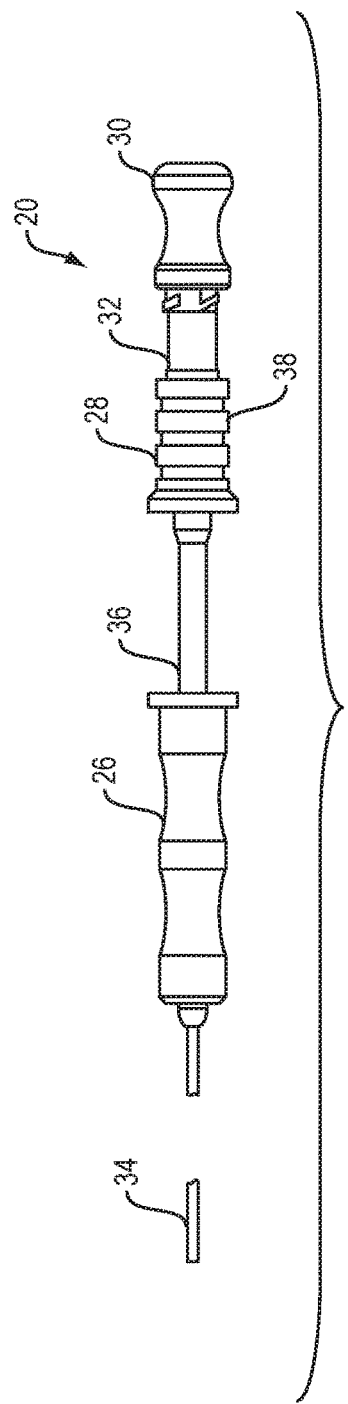
FIG. 1-1 illustrates a side view of an aspiration device in a deactivated state in accordance with principles of the prior art.
Figures 1, 2:
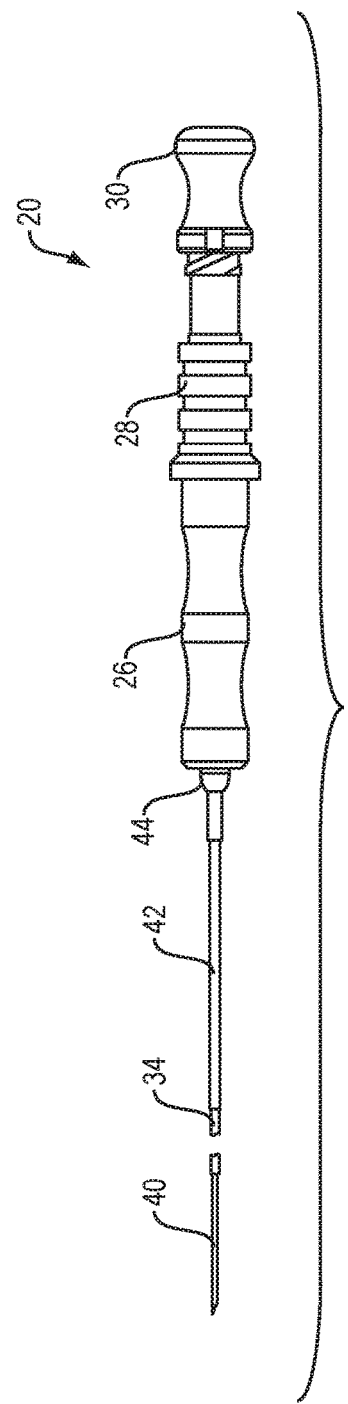

FIG. 1-1 illustrates an example needle aspiration device 20 (e.g., transbronchial needle aspiration (TBNA) device) in a deactivated position and FIG. 1-2 illustrates the device 20 in an activated position. The device 20 includes a handle body 26, a needle actuator 28, a stylet knob 30 and a Luer component 32. The handle body 26 is attached to a proximal end of a sheath 34. The needle actuator 28 includes a shaft portion 36 coupled to a handle portion 38. The needle actuator 28 is attached to a proximal end of a needle 40. The stylet knob 30 is attached to a proximal end of a stylet (not shown) received within the needle 40. The stylet knob 30 rotatably receives to a proximal end of the Luer component 32. A distal end of the Luer component 32 is attached to a cavity of the handle portion 38 of the needle actuator 28.

In the deactivated position, the distal end of the needle 40 is retracted within the sheath 34 (FIG. 1-1). In the activated position, the distal end of the needle 40 is exposed beyond the distal end of the sheath 34 (FIG. 1-2).

FIGS. 2.1-2.4 illustrate various views of a spacer/clamp (hereinafter clamp) 50 used to secure a needle aspiration device, such as the device 20 shown in FIGS. 1.1 and 1.2 in two different operational configurations. The clamp 50 includes a clamp and spacer section 52 and a handle section 54, both of which are coupled to a transition section 55. The clamp 50 may be formed of a monolithic material or may include separate components for each of the sections 52, 54 and 55. The clamp and spacer section 52 includes four semicircular arms 56, 58, 60 and 62. The four semicircular arms 56, 58, 60 and 62 include first ends that connect to or extend from the transition section 55 and include second ends that are unattached. The semicircular arms 56 and 58 are coplanar and the semicircular arms 60 and 62 are coplanar. A longitudinal axis 63 passes through a center of curvature of the arms 56 and 58 and a center of curvature of the arms 60 and 62. The longitudinal axis 63 is perpendicular to the planes of the arms 56, 58, 60 and 62.

The handle section 54 includes first and second handle grips 64 and 66. First ends of the first and second handle grips 64 and 66 are attached to or extend from an exterior surface of the transition section 55. The first and second handle grips 64 and 66 extend along different radials extending from the longitudinal axis 63. Compression of the first and second handle grips 64 and 66 toward each other causes the unattached ends of the semicircular arms 56 and 60 to move away from the unattached ends of the semicircular arms 58 and 62.

First locking tabs 76, 78, 80 and 82 are located near the unattached ends of the semicircular arms 56, 58, 60 and 62 on surfaces that face each other. The facing surfaces have normal vectors that are parallel to the longitudinal axis 63. The first locking tabs 76, 78, 80 and 82 help to keep the clamp 50 in place when used in the configuration shown below in FIG. 3, due to the size and/or configuration of the tabs 76, 78, 80 and 82.

The unattached ends of the semicircular arms 56, 58, 60 and 62 may include second locking tabs 84, 86, 88 and 89. The second locking tabs 84, 86, 88 and 89 include an edge adjacent to an interior surface of the semicircular arms 56, 58, 60 and 62 that is angularly different than the adjacent interior surface of the semicircular arms 56, 58, 60 and 62. The second locking tabs 84, 86, 88 and 89 help to keep the clamp 50 in place when used in the configuration shown below in FIG. 4, due to the size and/or configuration of the tabs.

Protrusions 70 and 72 are positioned along a portion of an exterior surface of the semicircular arms 58 and 62. The protrusions 70 and 72 are sized in order to create a predefined distance value between outer surfaces of the semicircular arms 56 and 60 and outer surfaces of the other semicircular arms 58 and 62. When the clamp 50 is placed to effect a deactivation state, the protrusions 70 and 72 create a predefined separation between a needle actuator and a sheath handle body, such that a needle attached to the needle actuator would be recessed within a sheath attached to the sheath handle body.

Figures 1, 2:
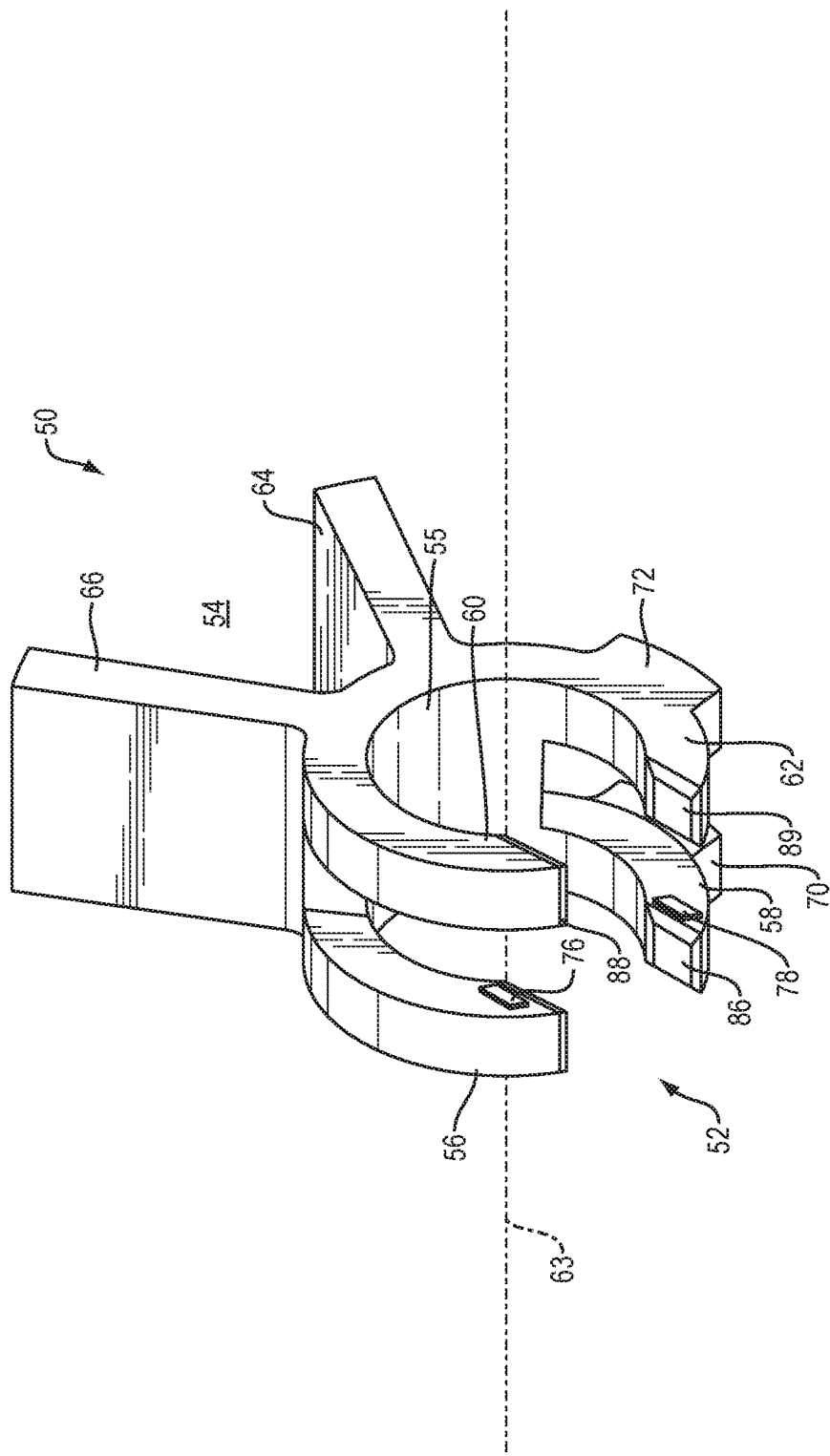
Figures 2, 3:
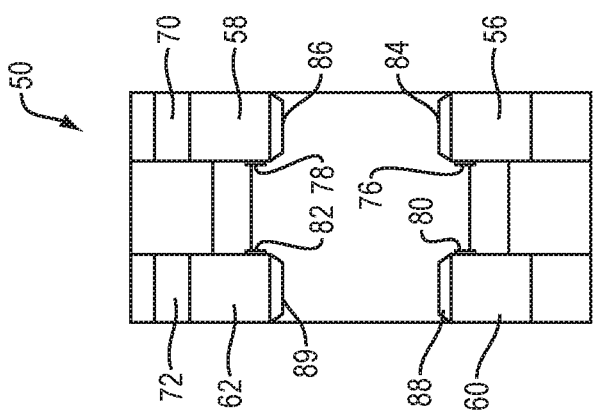

FIG. 3 shows a side view of a clamp 50-1 positioned along a shaft portion 36-1 of a needle actuator 28-1 of a needle aspiration device 20-1 in order to keep the needle that is connected to the shaft portion 36-1 and needle actuator 28-1 in a deactivated position. The needle actuator 28-1 includes an annular flange 90 located between the shaft portion 36-1 and a handle portion 38-1. A sheath handle body 26-1 includes an annular flange 92 located at the proximal end of the sheath handle body 26-1. When the clamp 50-1 is positioned in a needle safe mode (i.e., deactivated), the shaft portion 36-1 is received between the semicircular arms 56 and 60 and between the semicircular arms 58 and 62, such that a longitudinal axis of the shaft portion 36-1 is approximately perpendicular to a longitudinal axis of the semicircular arms 56, 58, 60 and 62. Exterior surfaces of the semicircular arms 56 and 60 make contact with a distal surface of the annular flange 90 and exterior surfaces of the protrusions 70 and 72 make contact with a proximal surface of the annular flange 92. The clamp 50-1 may be rotated 180 degrees and still perform the same functions.

The longitudinal distances between the inner surfaces of the semicircular arms 56 and 58 and the semicircular arms 60 and 62 are the same as or slightly greater that the diameter of the shaft portion 36-1 of the needle actuator 28-1. The first locking tabs 76 and 80 and the first locking tabs 78 and 82 reduce the longitudinal distance between the semicircular arms 56 and 60 and between the semicircular arms 58 and 62 in order to keep the shaft portion 36-1 from inadvertently sliding out of the clamp 50-1.

Figures 2, 3, 4:
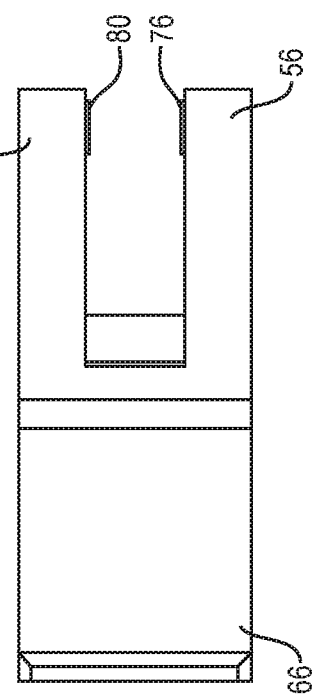
Figure 2:
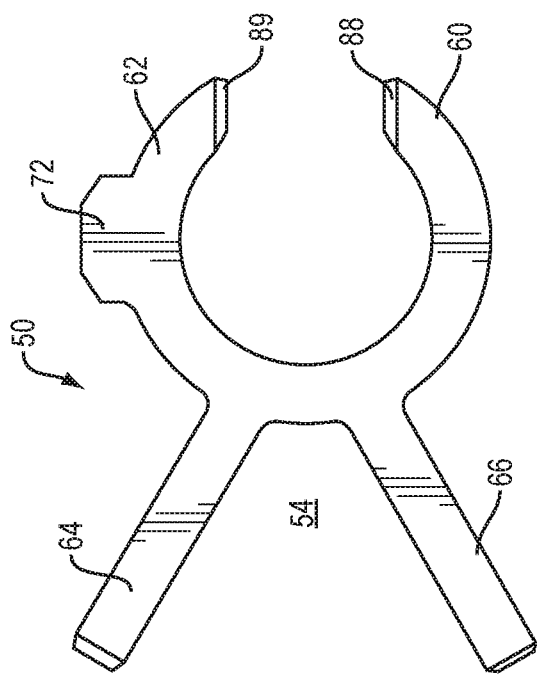

As shown in FIG. 4, the clamp 50-1 is placed around the needle actuator 28-1 and the sheath handle body 26-1 to keep the needle (not shown) that is attached to the needle actuator 28-1 in an activated position relative to the sheath (not shown) that is attached to the sheath handle body 26-1. In this activated position, the distal surface of the distal annular flange 90 of the needle actuator 28-1 is in contact with the proximal surface of the proximal annular flange 92 of the sheath handle body 26-1. Coplanar semicircular arms reside on a proximal side of the distal annular flange 90 and the other coplanar semicircular arms reside on a distal side of the proximal annular flange 92. The clamp 50-1 may be rotated 180 degrees. Portions of the distal annular flange 90 and the proximal annular flange 92 are maintained between interior surfaces of the semicircular arms having normal vectors parallel to a longitudinal axis of the needle aspiration device 20-1. Other interior surfaces of the semicircular arms that have normal vectors perpendicular to the longitudinal axis of the needle aspiration device 20-1 make at least partial contact with the exterior surfaces of the needle actuator 28-1 and the sheath handle body 26-1. Tabs keep the needle actuator 28-1 and the sheath handle body 26-1 from easily being separated from the clamp 50-1.

The clamp 50-1 includes grips 64-1 and 66-1 that allow for partial expansion of the arms. The expanded arms allow the needle actuator 28-1 and the sheath handle body 26-1 to be more easily received by the arms as shown in FIG. 4.

Figure 6:
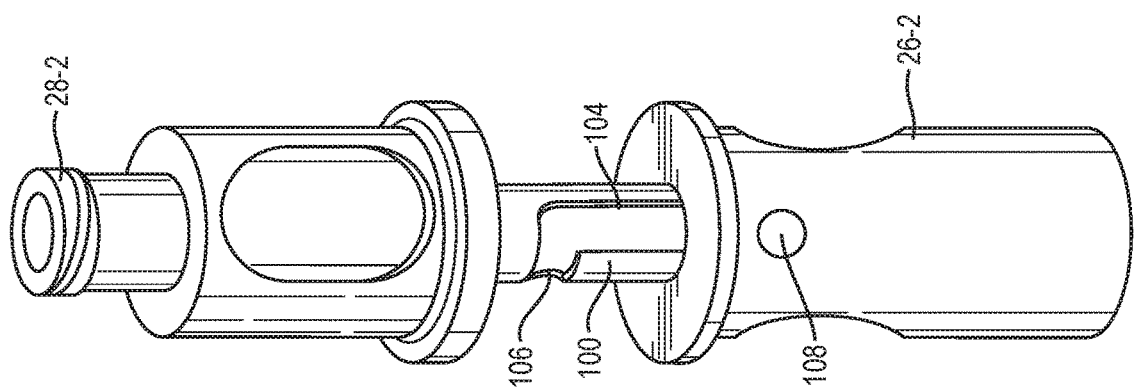
FIG. 6 illustrates a side view of the needle handle portion of FIG. 5 received within a sheath handle housing.
Figure 5:
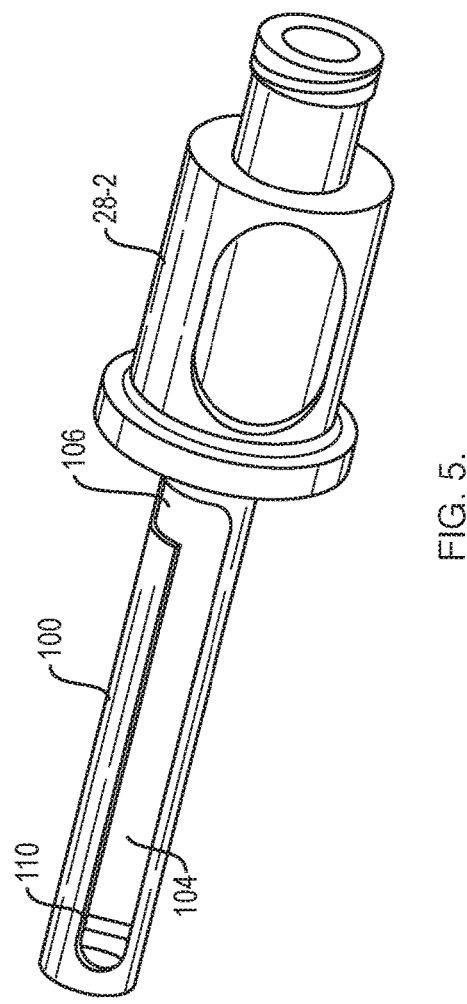
FIG. 5 illustrates a perspective view of a needle handle portion of an aspiration device formed in accordance with principles of the present invention.
Figure 7:
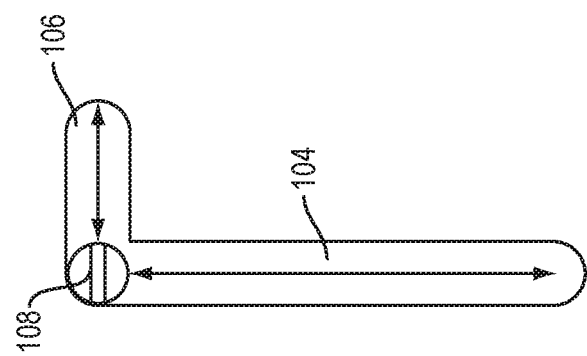
FIG. 7 illustrates interaction of a set screw of the sheath handle housing of FIG. 6 with a groove of the needle handle portion of FIG. 5.

FIGS. 5-7 illustrate an alternate embodiment for locking a needle in an activated state. FIG. 5 illustrates a needle actuator 28-2 that includes a needle handle shaft portion 100 having a locking device. The needle handle shaft portion 100 includes a longitudinal groove 104 that extends from a distal end to a proximal end of the needle handle shaft portion 100. The locking device includes a locking groove 106 that is opened on one side to the longitudinal groove 104. A distal end of the longitudinal groove 104 includes a feedback mechanism 110.

FIG. 6 shows the needle handle shaft portion 100 of the needle actuator 28-2 being received within a sheath handle body 26-2. The locking device also includes a set screw 108 or comparable device within the sheath handle body 26-2. The set screw 108 extends into a cavity/lumen of the sheath handle body 26-2. The set screw 108 is received within the longitudinal groove 104. The longitudinal groove 104 allows the needle actuator 28-2 to move in a longitudinal direction while avoiding rotation. After the needle actuator 28-2 is advanced distally relative to the shaft handle 26-2, the needle actuator 28-2 may be rotated such that the set screw 108 slides into the locking groove 106. The locking groove 106 keeps the needle actuator 28-2 from inadvertently being retracted proximally.

As the needle actuator 28-2 is retracted proximally relative to the shaft handle 26-2, the set screw 108 passes over the feedback mechanism 110. The feedback mechanism 110 may be a piece of the needle handle shaft portion 100 that may not flush to the exterior surface and is perpendicular to a major axis of the longitudinal groove 104. As the set screw 108 passes over the feedback mechanism 110, a sound and/or brief interruption in motion occurs (i.e., audible/tactile feedback), thus providing an indication to the user of the relative positions of the shaft handle 26-2 and the needle actuator 28-2.

EMBODIMENTS

A. A medical device comprising: a needle having a distal end and a proximal end; a sheath having a distal end and a proximal end; a sheath handle having a distal end and a proximal end, the sheath handle comprising a lumen extending from the proximal end to the distal end, wherein the distal end of the sheath handle is connected to the proximal end of the sheath; a needle actuator having a distal end and a proximal end, wherein the distal end of the needle actuator is connected to the proximal end of the needle; a locking device configured to restrict distal movement of the needle actuator relative to the sheath handle when the medical device is placed in one of two operational states.

B. The medical device of A, wherein a first one of the operational states is a deactivation state.

C. The medical device of B, wherein the deactivation state comprises the distal end of the needle being housed within the distal end of the sheath.

D. The medical device of any of B or C, wherein a second one of the operational states is an activation state.

E. The medical device of any of Claims A-D, wherein the locking device further comprises: a clamping element configured to restrict proximal movement of the needle actuator relative to the sheath handle when the medical device is in a first one of the operational states; and a spacing element configured to restrict distal movement of the needle actuator relative to the sheath handle when the medical device in a second one of the operational states.

F. The medical device of E, wherein the first operational state is a needle actuation state, wherein the distal end of the needle extends distally beyond the distal end of the sheath.

G. The medical device of F, wherein the clamping element and the spacing element are formed of a monolithic material.

H. The medical device of F or G, wherein the clamping element comprises: a base section; a first pair of curved arms that extend from the base section along a first plane; and a second pair of curved arms that extend from the base section along a second plane, wherein the radius of curvature of all the arms is based on a shape of an exterior of the needle actuator and the sheath handle, wherein an axis connecting a center of curvature of the first pair of curved arms and a center of curvature of the second pair of curved arms is perpendicular to the first and second planes.

I. The medical device of H, wherein the needle actuator comprises: a shaft portion; a handle portion; and a flange located between the shaft portion and the handle portion, wherein the sheath handle comprises a flange at the proximal end of the sheath handle, wherein a gap between the first pair of curved arms and the second pair of curved arms is based on the flanges of the needle actuator and the sheath handle.

J. The medical device of I, wherein the spacing element is configured to receive the shaft portion within the gap between the first pair of curved arms and the second pair of curved arms, such that exterior edges of a first one of the first pair of curved arms and a first one of the second pair of curved arms makes contact with one of the flange of the handle portion or the flange of the sheath handle and exterior edges of a second one of the first pair of curved arms and a second one of the second pair of curved arms makes contact with the other flange of the handle portion or the other flange of the sheath handle.

K. The medical device of J, wherein one of the exterior edges of the first one of the first pair of curved arms and the first one of the second pair of curved arms or the exterior edges of the second one of the first pair of arms and the second one of the second curved arms comprises an extension based upon a deactivation state position of the needle actuator relative to the sheath handle.

L. The medical device of J or K, wherein the locking device further comprises a handle component connected at least in part to the base section, wherein activation of the handle component translates to an expansion motion of the first ones of the first and second pairs of curved arms from the second ones of the first and second pairs of curved arms.

M. The medical device of J-L, wherein an end of at least one of the curved arms comprises a tab configured to limit inadvertent movement of the needle actuator and the sheath handle when in an activation state.

N. The medical device of J-M, wherein an edge of at least one of the curved arms that makes contact with the shaft portion during a deactivation state comprises a tab configured to limit inadvertent movement of the shaft portion.

O. The medical device of A, wherein the needle actuator comprises: a handle portion; and a shaft portion comprising a first groove that extends longitudinally, wherein the locking device comprises: an element that protrudes at least partially into a lumen of the sheath handle; and a second groove on the shaft portion that links to the first groove near a proximal end of the shaft portion, wherein the first and second grooves are configured to receive the protruding element, wherein the second groove limits movement of the protruding element.

P. The medical device of O, wherein the first groove comprises a feedback feature configured to provide at least one of an audible feedback or a tactile feedback as the needle actuator is moved distally relative to the sheath handle.

Q. A spacer and clamp device for a needle aspiration device having a sheath handle and a needle handle, the spacer and clamp device comprising: a spacing element configured to restrict distal movement of the needle handle relative to the sheath handle when the needle aspiration device is in a first one of a plurality of operational states; and a clamping element configured to restrict proximal movement of the needle handle relative to the sheath handle when the needle aspiration device is in a second one of the operational states, the clamping element comprising: a base section; a first pair of curved arms that extend from the base section in a first plane; and a second pair of curved arms that extend from the base section in a second plane, wherein the radius of curvature of all the arms is based on a shape of an exterior of the needle handle and the sheath handle, wherein an axis connecting a center of curvature of the first pair of curved arms and a center of curvature of the second pair of curved arms is perpendicular to the first and second planes.

R. The spacer and clamp device of Q, wherein the spacing element is configured to receive a shaft portion of the needle handle within a gap between the first pair of curved arms and the second pair of curved arms, such that exterior edges of a first one of the first pair of curved arms and a first one of the second pair of curved arms makes contact with one of a flange of the handle portion or a flange of the sheath handle and exterior edges of a second one of the first pair of curved arms and a second one of the second pair of curved arms makes contact with the other flange of the handle portion or the other flange of the sheath handle, S. The spacer and clamp device of Q or R, wherein the clamping element further comprises a grip component connected at least in part to the base section, wherein activation of the grip component translates to an expansion motion of first ones of the first and second pairs of curved arms from second ones of the first and second pairs of curved arms.

T. The medical device of any of R-S, wherein one of the exterior edges of a first one of the first pair of curved arms and a first one of the second pair of curved arms or the exterior edges of a second one of the first pair of arms and a second one of the second curved arms comprises an extension based upon a deactivation state position of the needle actuator relative to the sheath handle, wherein one of the edges of at least one of the curved arms that makes contact with the shaft portion during a deactivation state comprises a tab configured to limit inadvertent movement of the shaft portion.

The description of the invention is merely exemplary in nature and variations that do not depart from the gist of the invention are intended to be within the scope of the invention. Such variations are not to be regarded as a departure from the spirit and scope of the invention.

What is claimed is:
1. A medical device comprising:
   a needle having a distal end and a proximal end;
   a sheath having a distal end and a proximal end, the sheath being configured to slidably receive the needle;
   a sheath handle having a distal end and a proximal end, the sheath handle comprising a lumen extending from the proximal end to the distal end, wherein the distal end of the sheath handle is connected to the proximal end of the sheath;
   a needle actuator having a distal end and a proximal end, wherein the distal end of the needle actuator is connected to the proximal end of the needle; and
   a lock configured to: (i) restrict distal movement of the needle actuator relative to the sheath handle when the medical device is placed in a first operational state, and (ii) restrict proximal movement of the needle actuator relative to the sheath handle when the medical device is placed in a second operational state that is different than the first operational state.
2. The medical device of claim 1, wherein the first operational state is a deactivation state.
3. The medical device of claim 2, wherein the deactivation state comprises the distal end of the needle being housed within the distal end of the sheath.
4. The medical device of claim 2, wherein the second operational state is an activation state.
5. The medical device of claim 1, wherein the lock further comprises:

a clamping element configured to restrict proximal movement of the needle actuator relative to the sheath handle when the medical device is in the first operational state; and
a spacing element configured to restrict distal movement of the needle actuator relative to the sheath handle when the medical device in the second operational state.

6. The medical device of claim 5, wherein the first operational state is a needle actuation state, wherein the distal end of the needle extends distally beyond the distal end of the sheath.

7. The medical device of claim 6, wherein the clamping element and the spacing element are formed of a monolithic material.

8. The medical device of claim 6, wherein the clamping element comprises:
   a base section;
   a first pair of curved arms that extend from the base section along a first plane; and
   a second pair of curved arms that extend from the base section along a second plane,
   wherein the radius of curvature of all the arms is based on a shape of an exterior of the needle actuator and the sheath handle,
   wherein an axis connecting a center of curvature of the first pair of curved arms and a center of curvature of the second pair of curved arms is perpendicular to the first and second planes.

9. The medical device of claim 8, wherein the needle actuator comprises:
   a shaft portion;
   a handle portion; and
   a flange located between the shaft portion and the handle portion,
   wherein the sheath handle comprises a flange at the proximal end of the sheath handle,
   wherein a gap between the first pair of curved arms and the second pair of curved arms is based on the flanges of the needle actuator and the sheath handle.

10. The medical device of claim 9, wherein the spacing element is configured to receive the shaft portion within the gap between the first pair of curved arms and the second pair of curved arms, such that exterior edges of a first one of the first pair of curved arms and a first one of the second pair of curved arms makes contact with one of the flange of the handle portion or the flange of the sheath handle and exterior edges of a second one of the first pair of curved arms and a second one of the second pair of curved arms makes contact with the other flange of the handle portion or the other flange of the sheath handle.

11. The medical device of claim 10, wherein one of the exterior edges of the first one of the first pair of curved arms and the first one of the second pair of curved arms or the exterior edges of the second one of the first pair of arms and the second one of the second curved arms comprises an extension based upon a deactivation state position of the needle actuator relative to the sheath handle.

12. The medical device of claim 10, wherein the lock further comprises a handle component connected at least in part to the base section, wherein activation of the handle component translates to an expansion motion of the first ones of the first and second pairs of curved arms from second ones of the first and second pairs of curved arms.

13. The medical device of claim 10, wherein an end of at least one of the curved arms comprises a tab configured to limit inadvertent movement of the needle actuator and the sheath handle when in an activation state.

14. The medical device of claim 10, wherein an edge of at least one of the curved arms that makes contact with the shaft portion during a deactivation state comprises a tab configured to limit inadvertent movement of the shaft portion.

15. The medical device of claim 1, wherein the needle actuator comprises:
   a handle portion; and
   a shaft portion comprising a first groove that extends longitudinally,
   wherein the lock comprises:
      an element that protrudes at least partially into a lumen of the sheath handle; and
      a second groove on the shaft portion that links to the first groove near a proximal end of the shaft portion,
   wherein the first and second grooves are configured to receive the protruding element,
   wherein the second groove limits movement of the protruding element.

16. The medical device of claim 15, wherein the first groove comprises a feedback feature configured to provide at least one of an audible feedback or a tactile feedback as the needle actuator is moved relative to the sheath handle.

17. A spacer and clamp device for a needle aspiration device having a sheath handle and a needle handle, the spacer and clamp device comprising:
   a spacing element configured to restrict distal movement of the needle handle relative to the sheath handle when the needle aspiration device is in a first one of a plurality of operational states; and
   a clamping element configured to restrict proximal movement of the needle handle relative to the sheath handle when the needle aspiration device is in a second one of the operational states, the clamping element comprising:
      a base section;
      a first pair of curved arms that extend from the base section in a first plane; and
      a second pair of curved arms that extend from the base section in a second plane,
   wherein the radius of curvature of all the arms is based on a shape of an exterior of the needle handle and the sheath handle,
   wherein an axis connecting a center of curvature of the first pair of curved arms and a center of curvature of the second pair of curved arms is perpendicular to the first and second planes.

18. The spacer and clamp device of claim 17, wherein the spacing element is configured to receive a shaft portion of the needle handle within a gap between the first pair of curved arms and the second pair of curved arms, such that exterior edges of a first one of the first pair of curved arms and a first one of the second pair of curved arms makes contact with one of a flange of the handle portion or a flange of the sheath handle and exterior edges of a second one of the first pair of curved arms and a second one of the second pair of curved arms makes contact with the other flange of the handle portion or the other flange of the sheath handle.

19. The spacer and clamp device of claim 17, wherein the clamping element further comprises a grip component connected at least in part to the base section, wherein activation of the grip component translates to an expansion motion of first ones of the first and second pairs of curved arms from second ones of the first and second pairs of curved arms.

20. The spacer and clamp device of claim 17, wherein one of the exterior edges of a first one of the first pair of curved arms and a first one of the second pair of curved arms or the exterior edges of a second one of the first pair of arms and a second one of the second curved arms comprises an extension based upon a deactivation state position of the needle actuator relative to the sheath handle,
   wherein one of the edges of at least one of the curved arms that makes contact with the shaft portion during a deactivation state comprises a tab configured to limit inadvertent movement of the shaft portion.

* * * * *